(12) United States Patent
Thomas et al.

(10) Patent No.: US 9,750,595 B2
(45) Date of Patent: Sep. 5, 2017

(54) IMPLANTABLE MEDICAL DEVICES WHICH INCLUDE GRIP-MEMBERS AND METHODS OF USE THEREOF

(71) Applicant: Covidien LP, Mansfield, MA (US)

(72) Inventors: Jonathan Thomas, New Haven, CT (US); Ferass Abuzaina, Shelton, CT (US)

(73) Assignee: Covidien LP, Mansfield, MA (US)

( * ) Notice: Subject to any disclaimer, the term of this patent is extended or adjusted under 35 U.S.C. 154(b) by 462 days.

(21) Appl. No.: 14/023,503

(22) Filed: Sep. 11, 2013

(65) Prior Publication Data

US 2014/0094831 A1 Apr. 3, 2014

Related U.S. Application Data

(60) Provisional application No. 61/706,899, filed on Sep. 28, 2012.

(51) Int. Cl.
*A61F 2/00* (2006.01)
*D04B 21/12* (2006.01)

(52) U.S. Cl.
CPC ............ *A61F 2/0063* (2013.01); *D04B 21/12* (2013.01); *D10B 2501/0632* (2013.01); *D10B 2509/08* (2013.01); *F04C 2270/0421* (2013.01)

(58) Field of Classification Search
CPC ....... A61F 2/0063; A61B 17/04; A61B 17/08; A61B 2017/081; A61B 2017/086; A61B 2017/088; D10F 2/0063; Y10T 428/24017; Y10T 428/24008; A44B 18/0015; A44B 18/0038; A44B 18/0061; D10B 2501/063; D10B 2501/0632; D10B 2509/08; D10B 2509/02; D10B 2509/022

USPC ........ 428/100; 606/151, 213, 215, 214, 216, 606/217; 623/23.72, 23, 74; 602/36, 37, 602/78

See application file for complete search history.

(56) References Cited

U.S. PATENT DOCUMENTS

| 3,166,072 | A | | 1/1965 | Sullivan, Jr. | |
|---|---|---|---|---|---|
| 3,320,649 | A | | 5/1967 | Naimer | |
| 3,494,006 | A | | 2/1970 | Brumlik | |
| 3,522,637 | A | * | 8/1970 | Brumlik | A44B 18/0015 24/445 |
| 3,845,641 | A | * | 11/1974 | Waller | A44B 18/0038 26/9 |
| 3,874,388 | A | | 4/1975 | King et al. | |
| 3,981,051 | A | * | 9/1976 | Brumlik | A44B 18/0015 24/447 |

(Continued)

FOREIGN PATENT DOCUMENTS

| CN | 87108125 A | 9/1988 |
|---|---|---|
| CN | 101355907 A | 1/2009 |

(Continued)

OTHER PUBLICATIONS

Extended European Search Report, corresponding to European Application No. 13 18 6535.4, dated Nov. 28, 2013; (7 Pages).

(Continued)

*Primary Examiner* — Elizabeth Houston
*Assistant Examiner* — Charles Wei (57) ABSTRACT

The present disclosure relates to implantable medical devices which include grip-members and methods of reinforcing tissue with such devices.

20 Claims, 6 Drawing Sheets

(56) References Cited

U.S. PATENT DOCUMENTS

| | | | |
|---|---|---|---|
| 4,259,959 A | 4/1981 | Walker | |
| 4,338,800 A | 7/1982 | Matsuda | |
| 4,414,720 A | 11/1983 | Crooms | |
| 4,421,807 A * | 12/1983 | Clausing | E04D 5/10 428/192 |
| 4,548,202 A | 10/1985 | Duncan | |
| 4,589,416 A | 5/1986 | Green | |
| 4,632,097 A | 12/1986 | Brooks | |
| 4,709,562 A | 12/1987 | Matsuda | |
| 4,816,339 A | 3/1989 | Tu et al. | |
| 4,825,866 A * | 5/1989 | Pierce | A61B 17/085 606/216 |
| 4,854,316 A * | 8/1989 | Davis | A61F 2/0063 128/898 |
| 4,881,546 A | 11/1989 | Kaessmann | |
| 5,013,316 A | 5/1991 | Goble et al. | |
| 5,081,714 A | 1/1992 | Liu | |
| 5,147,374 A * | 9/1992 | Fernandez | A61F 2/0063 606/151 |
| 5,171,252 A | 12/1992 | Friedland | |
| 5,224,946 A | 7/1993 | Hayhurst et al. | |
| 5,234,462 A * | 8/1993 | Pavletic | A61B 17/085 606/215 |
| 5,236,445 A | 8/1993 | Hayhurst et al. | |
| 5,254,127 A * | 10/1993 | Wholey | A61B 17/11 285/397 |
| 5,254,133 A | 10/1993 | Seid | |
| 5,258,016 A | 11/1993 | DiPoto et al. | |
| 5,342,376 A | 8/1994 | Ruff | |
| 5,342,393 A | 8/1994 | Stack | |
| 5,354,298 A | 10/1994 | Lee et al. | |
| 5,356,432 A * | 10/1994 | Rutkow | A61B 17/0057 600/37 |
| 5,368,549 A | 11/1994 | McVicker | |
| 5,378,522 A * | 1/1995 | Lagomarsino | A44B 18/0069 24/306 |
| 5,380,334 A | 1/1995 | Torrie et al. | |
| 5,383,897 A | 1/1995 | Wholey | |
| 5,403,326 A | 4/1995 | Harrison et al. | |
| 5,417,699 A | 5/1995 | Klein et al. | |
| 5,423,856 A | 6/1995 | Green | |
| 5,423,885 A | 6/1995 | Williams | |
| 5,458,609 A | 10/1995 | Gordon et al. | |
| 5,462,561 A | 10/1995 | Voda | |
| 5,480,403 A | 1/1996 | Lee et al. | |
| 5,489,298 A | 2/1996 | Love et al. | |
| 5,527,321 A | 6/1996 | Hinchliffe | |
| 5,540,704 A | 7/1996 | Gordon et al. | |
| 5,569,273 A | 10/1996 | Titone et al. | |
| 5,571,116 A | 11/1996 | Bolanos et al. | |
| 5,584,859 A | 12/1996 | Brotz | |
| 5,601,558 A | 2/1997 | Torrie et al. | |
| 5,639,276 A | 6/1997 | Weinstock et al. | |
| 5,643,320 A | 7/1997 | Lower et al. | |
| 5,667,513 A | 9/1997 | Torrie et al. | |
| 5,683,417 A | 11/1997 | Cooper | |
| 5,697,978 A | 12/1997 | Sgro | |
| 5,700,273 A | 12/1997 | Buelna et al. | |
| 5,702,421 A | 12/1997 | Schneidt | |
| 5,713,903 A | 2/1998 | Sander et al. | |
| 5,716,409 A | 2/1998 | Debbas | |
| 5,720,753 A | 2/1998 | Sander et al. | |
| 5,766,234 A | 6/1998 | Chen et al. | |
| 5,779,719 A | 7/1998 | Klein et al. | |
| 5,797,960 A | 8/1998 | Stevens et al. | |
| 5,810,847 A | 9/1998 | Laufer et al. | |
| 5,823,956 A | 10/1998 | Roth et al. | |
| 5,824,082 A | 10/1998 | Brown | |
| 5,829,447 A | 11/1998 | Stevens et al. | |
| 5,836,955 A | 11/1998 | Buelna et al. | |
| D404,128 S | 1/1999 | Huebner | |
| 5,855,614 A | 1/1999 | Stevens et al. | |
| 5,868,749 A | 2/1999 | Reed | |
| 5,895,404 A | 4/1999 | Ruiz | |
| 5,916,224 A | 6/1999 | Esplin | |
| 5,928,244 A | 7/1999 | Tovey et al. | |
| 5,944,739 A | 8/1999 | Zlock et al. | |
| 5,948,000 A | 9/1999 | Larsen et al. | |
| 5,948,001 A | 9/1999 | Larsen | |
| 5,957,916 A | 9/1999 | Jeevanandam et al. | |
| 5,968,047 A | 10/1999 | Reed | |
| 5,972,007 A | 10/1999 | Sheffield et al. | |
| 5,993,459 A | 11/1999 | Larsen et al. | |
| 6,004,333 A | 12/1999 | Sheffield et al. | |
| 6,013,083 A | 1/2000 | Bennett | |
| 6,018,852 A * | 2/2000 | Coslovi | A44B 18/003 24/304 |
| 6,036,690 A | 3/2000 | De La Plaza Fernandez | |
| 6,042,534 A | 3/2000 | Gellman et al. | |
| 6,066,776 A | 5/2000 | Goodwin et al. | |
| 6,066,777 A | 5/2000 | Renchetrit | |
| 6,068,648 A | 5/2000 | Cole et al. | |
| 6,074,395 A | 6/2000 | Trott et al. | |
| 6,079,414 A | 6/2000 | Roth | |
| 6,086,591 A | 7/2000 | Bojarski | |
| 6,120,539 A | 9/2000 | Eldridge et al. | |
| 6,146,387 A | 11/2000 | Trott et al. | |
| 6,152,144 A | 11/2000 | Lesh et al. | |
| 6,165,183 A | 12/2000 | Kuehn et al. | |
| 6,174,320 B1 | 1/2001 | Kugel et al. | |
| 6,206,886 B1 | 3/2001 | Bennett | |
| 6,231,561 B1 | 5/2001 | Frazier et al. | |
| 6,241,768 B1 | 6/2001 | Agarwal et al. | |
| 6,245,079 B1 | 6/2001 | Nobles et al. | |
| 6,258,124 B1 | 7/2001 | Darois et al. | |
| 6,269,819 B1 | 8/2001 | Oz et al. | |
| 6,270,515 B1 | 8/2001 | Linden et al. | |
| 6,280,448 B1 | 8/2001 | Trott et al. | |
| 6,287,316 B1 | 9/2001 | Agarwal et al. | |
| 6,290,674 B1 | 9/2001 | Roue et al. | |
| 6,290,702 B1 | 9/2001 | Fucci et al. | |
| 6,311,623 B1 | 11/2001 | Zaruba | |
| 6,334,873 B1 | 1/2002 | Lane et al. | |
| 6,346,074 B1 | 2/2002 | Roth | |
| 6,346,109 B1 | 2/2002 | Fucci et al. | |
| 6,355,030 B1 | 3/2002 | Aldrich et al. | |
| 6,363,940 B1 | 4/2002 | Krag | |
| 6,368,339 B1 | 4/2002 | Amplatz | |
| 6,383,201 B1 | 5/2002 | Dong | |
| 6,386,242 B1 * | 5/2002 | Higashinaka | A44B 18/0038 139/391 |
| 6,408,656 B1 | 6/2002 | Ory et al. | |
| 6,425,924 B1 * | 7/2002 | Rousseau | A61B 17/0057 606/151 |
| 6,428,550 B1 | 8/2002 | Vargas et al. | |
| 6,443,964 B1 | 9/2002 | Ory et al. | |
| 6,485,503 B2 | 11/2002 | Jacobs et al. | |
| 6,517,584 B1 | 2/2003 | Lecaive | |
| 6,551,356 B2 | 4/2003 | Rousseau | |
| 6,565,943 B1 * | 5/2003 | Kondo | A44B 18/003 24/442 |
| 6,575,988 B2 | 6/2003 | Rousseau | |
| 6,596,002 B2 | 7/2003 | Therin et al. | |
| 6,599,323 B2 | 7/2003 | Melican et al. | |
| 6,638,284 B1 | 10/2003 | Rousseau et al. | |
| 6,645,226 B1 | 11/2003 | Jacobs et al. | |
| 6,669,735 B1 * | 12/2003 | Pelissier | A61F 2/0063 606/151 |
| 6,685,714 B2 | 2/2004 | Rousseau | |
| 6,726,706 B2 * | 4/2004 | Dominguez | A61B 17/0466 606/148 |
| 6,755,867 B2 | 6/2004 | Rousseau | |
| 6,755,868 B2 * | 6/2004 | Rousseau | A61F 2/0063 606/151 |
| 6,800,082 B2 | 10/2004 | Rousseau | |
| 6,872,227 B2 | 3/2005 | Sump et al. | |
| 6,991,643 B2 | 1/2006 | Saadat | |
| 7,112,209 B2 | 9/2006 | Ramshaw et al. | |
| 7,131,944 B2 | 11/2006 | Jacquetin | |
| 7,331,199 B2 | 2/2008 | Ory et al. | |
| 7,662,169 B2 * | 2/2010 | Wittmann | A61B 17/00234 606/215 |

(56) References Cited

U.S. PATENT DOCUMENTS

| | | | |
|---|---|---|---|
| 7,875,074 B2* | 1/2011 | Chen | A61F 2/12 600/37 |
| 7,985,173 B2 | 7/2011 | Jacquetin | |
| 8,062,331 B2* | 11/2011 | Zamierowski | A61B 17/064 602/43 |
| 8,206,632 B2 | 6/2012 | Rousseau et al. | |
| 8,388,633 B2 | 3/2013 | Rousseau et al. | |
| 8,500,759 B2 | 8/2013 | Koyfman et al. | |
| 8,506,582 B2 | 8/2013 | Kammerer et al. | |
| 8,579,990 B2 | 11/2013 | Priewe | |
| 2001/0044637 A1 | 11/2001 | Jacobs et al. | |
| 2001/0051815 A1 | 12/2001 | Esplin | |
| 2002/0022861 A1 | 2/2002 | Jacobs et al. | |
| 2002/0029063 A1 | 3/2002 | Wittmann | |
| 2002/0035361 A1 | 3/2002 | Houser et al. | |
| 2002/0038151 A1* | 3/2002 | Plouhar | A61F 2/0063 623/23.72 |
| 2002/0042621 A1 | 4/2002 | Liddicoat et al. | |
| 2002/0077661 A1* | 6/2002 | Saadat | A61B 17/08 606/221 |
| 2002/0087049 A1 | 7/2002 | Brock et al. | |
| 2002/0087166 A1 | 7/2002 | Brock et al. | |
| 2002/0087169 A1 | 7/2002 | Brock et al. | |
| 2002/0095167 A1 | 7/2002 | Liddicoat et al. | |
| 2002/0095175 A1 | 7/2002 | Brock et al. | |
| 2002/0183768 A1 | 12/2002 | Deem et al. | |
| 2004/0039415 A1* | 2/2004 | Zamierowski | A61B 17/064 606/215 |
| 2005/0021058 A1* | 1/2005 | Negro | A61F 2/0063 606/151 |
| 2005/0177190 A1* | 8/2005 | Zamierowski | A61B 17/064 606/215 |
| 2005/0182445 A1* | 8/2005 | Zamierowski | A61B 17/064 606/213 |
| 2005/0234510 A1* | 10/2005 | Zamierowski | A61B 17/064 606/215 |
| 2005/0240220 A1* | 10/2005 | Zamierowski | A61B 17/064 606/215 |
| 2005/0246873 A1* | 11/2005 | Tachauer | A44B 18/0061 24/451 |
| 2009/0012543 A1 | 1/2009 | Kansoul | |
| 2011/0282365 A1* | 11/2011 | Hadba | A61L 31/06 606/151 |

FOREIGN PATENT DOCUMENTS

| | | |
|---|---|---|
| EP | 2 229 918 A1 | 9/2010 |
| EP | 2 404 571 A1 | 1/2012 |
| WO | WO 03/105703 A2 | 12/2003 |
| WO | WO 2012/021600 A1 | 2/2012 |

OTHER PUBLICATIONS

Chinese Office Action issued Oct. 28, 2016 in corresponding Chinese Patent Application No. 201310456246.5, together with English translation, 14 pages.

* cited by examiner

IMPLANTABLE MEDICAL DEVICES WHICH INCLUDE GRIP-MEMBERS AND METHODS OF USE THEREOF

CROSS-REFERENCE TO RELATED APPLICATIONS

This application claims the benefit of and priority to U.S. Provisional Patent Application No. 61/706,899, filed Sep. 28, 2012, the entire disclosure of which is incorporated by reference herein.

BACKGROUND

Technical Field

The present disclosure relates generally to implantable medical devices having at least one biocompatible substrate including a first surface and a second surface, wherein the first and second surface each include at least one grip-member.

Background of Related Art

Several types of wound closure devices and methods are known, and may include sutures, staples, and surgical mesh. Application of most of these wound closure devices may be time consuming, and may require considerable manual dexterity and patience. In addition, while these methods may be functionally adequate, some may take too long to provide effective wound closure, or be cosmetically unappealing.

Most prevalent is the use of needles and sutures. Sutures provide high tensile strength, a low incidence of reopening, and can provide minimal cosmetic scarring. However, the application of sutures may be time-consuming and may inflict additional trauma to the tissue after each passing of the needle.

Surgical staples may be applied more rapidly than sutures; however, staples may also inflict additional trauma to the tissue and also may display a higher risk of the tissue opening.

Surgical mesh have also been used in combination with sutures and staples to reinforce a wound. Prior art mesh may often be affixed to a tissue with a suture or staple and may only provide support in a single plane, directly beneath the wound. In wounds that span two or more planes of tissue, such a mesh may fail to adequately fill the wound and thus allows dead space to exist between the multiple layers of tissue. It is believed that wounds which are not adequately filled or include dead-space may promote seroma formation.

Thus, it would be beneficial to provide implantable medical devices which can attach to multiple layers of tissue. In addition, it would be beneficial to provide implantable medical devices which can attach directly to tissue with and/or without the use of an additional surgical fastener, such as a suture, staple, and the like, thereby reducing trauma inflicted to the reinforced tissue layers.

It would be further beneficial to provide implantable medical device which can adequately fill an opening in two or more planes of tissue such that dead space between the multi-planes of tissue maybe significantly reduced and the opportunity for seroma formation also reduced.

SUMMARY

The present disclosure describes implantable medical devices which include a first substrate having a first and second surface wherein each surface includes at least one grip-member to help attach the implant to tissue.

In certain embodiments, the implantable medical devices for supporting tissue in multiple planes include a first substrate and second substrate, the first substrate having a first surface including a plurality of first grip-members and a second surface including a plurality of second grip-members; and, the second substrate having a third surface including a plurality of third grip-members and a fourth surface including a plurality of fourth grip-members, wherein the first substrate is attached to the second substrate via the second and third grip-members. In embodiments, the first and second substrates may be removably attached to one another via the grip-members.

Methods of reinforcing multiple planes of tissue during a surgical procedure are also disclosed. In embodiments, methods of reinforcing tissue include, providing at least one implantable medical device comprising a first substrate having a first surface including a plurality of first grip-members and a second surface including a plurality of second grip-members; and, a second substrate having a third surface including a plurality of third grip-members and a fourth surface including a plurality of fourth grip-members, wherein the first substrate is attached to the second substrate via the second and third grip-members; and, positioning the at least one implantable medical device between two or more layers of tissue.

BRIEF DESCRIPTION OF THE DRAWINGS

The accompanying drawings, which are incorporated in and constitute a part of the specification, illustrate embodiments of the disclosure and, together with a general description of the disclosure given above, and the detailed description of the embodiments given below, serve to explain the principles of the disclosure.

DETAILED DESCRIPTION

The present disclosure relates to implantable medical devices which display tissue-gripping capabilities. In embodiments, the implantable medical devices include at least one biocompatible substrate having at least a first and second surface wherein the each of the first and second surfaces include grip-members. In embodiments, the first and second surfaces may be on opposite portions of the biocompatible substrate, e.g., the grip-members may be on a top surface and a bottom surface of the substrate. In embodiments, the biocompatible substrates are porous. In embodiments, the first biocompatible substrate comprises a mesh.

The present disclosure also relates to implantable medical devices which include more than one biocompatible substrate. In embodiments, the implantable medical devices described herein may be multi-planar and include a first substrate and a second substrate, the first substrate having a first and second surface, the first surface including a plurality of first grip-members and the second surface includes a plurality of second grip-members. The second substrate having a third and fourth surface, the third surface including a plurality of third grip-members, and the fourth surface including a plurality of fourth grip-members, wherein one of the first and second grip-members are attached to one of the third and fourth grip-members to connect the first and second substrates.

In embodiments, at least one of the biocompatible substrates may comprise a mesh. In embodiments, at least one of the biocompatible substrates may be in a planar configuration. In embodiments, at least one of the biocompatible substrates may comprise a non-planar configuration, e.g., a conical configuration. In embodiments, more than two biocompatible substrates may be used to form a multi-planar implantable medical device.

The implants described herein may be used for reinforcing tissue, and in particularly, reinforcing tissue between multiple tissue planes. For example, the implants may be useful in reinforcing tissues in surgical procedures such as abdominoplasty, breast reconstruction, midline closures, lateral closures, hernia repair, retrorectus hernia repair, Rives-Stoppa procedures, incisional hernias, cosmetic surgery, and the like. It is envisioned that the implants described herein may be used to fill openings in multiple planes of tissue which decreases the likelihood of creating dead-space in at least one of the planes of the tissue. It is further envisioned that a decrease in dead-space between tissue planes may greatly reduce the likelihood of seroma formation.

In many surgical procedures, and particularly abdominoplasty, breast reconstruction, midline closures, lateral closures, and hernia repairs, surgeons may attempt to attach soft tissue layers to fascia layers via sutures which can be a time-consuming activity. Thus it is envisioned that the utilization of the self-gripping multi-planar implants described herein may reduce the time needed for stitching, reduce the dead space between multiple planes of tissue, and more adequately support and/or reinforce the approximated multi-planar tissues. In addition, since a portion of each of the multi-planar implants described herein may be positioned within each layer of wound which spans multiple layers, the tension and/or stress needed to maintain the tissue approximated is no longer applied to a single layer of tissue or a single planar substrate but rather spread across multiple layers of tissue by the multi-planar implant.

The multi-planar implants include at least one substrate and more particularly at least two substrates. Any biocompatible material may be used to form the biocompatible substrates and/or the filaments described herein. For example, the substrate may be made from natural, synthetic, bioabsorbable or non-bioabsorbable materials. It should of course be understood that any combination of natural, synthetic, bioabsorbable and non-bioabsorbable materials may be used to form the substrates or filaments described herein.

The term "bioabsorbable" as used herein is defined to include both biodegradable and bioresorbable materials. By bioabsorbable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

Representative natural bioabsorbable materials include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic bioabsorbable polymers include polyhydroxy acids prepared from lactone monomers, such as glycolide, lactide, caprolactone, $\epsilon$-caprolactone, valerolactone, and $\delta$-valerolactone, as well as pluronics, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly (hydroxyvaleric acid); poly(lactide-co-($\epsilon$-caprolactone-)); poly(glycolide-co-($\epsilon$-caprolactone)); polycarbonates; poly (pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof. In certain embodiments, the biocompatible substrate(s) may be formed using a combination of bioabsorbable and non-bioabsorbable polymers.

Some non-limiting examples of suitable non-bioabsorbable materials include polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, including expanded polytetrafluoroethylene (ePTFE) and condensed polytetrafluoroethylene c(PTFE), fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

Some examples of suitable biocompatible substrates include films, foams, meshes, buttresses, patches, tapes, pledgets, occlusion devices, and the like. In certain embodiments, the biocompatible substrate is a surgical mesh.

The biocompatible substrates may be formed using any method within the purview of those skilled in the art. Some non-limiting examples include, weaving, knitting, braiding, crocheting, extruding, spraying, casting, molding, and combinations thereof. In some embodiments, the biocompatible substrate may be a two or three dimensional surgical mesh which is woven, knitted, braided, or crocheted from at least one first filament to form the substrate. The at least one filament may be a monofilament or a multifilament. In certain embodiments, the biocompatible substrate may be a surgical mesh consisting of at least one first filament made of polyethylene terephthalate.

The grip-members described herein, which are positioned on at least a portion of the biocompatible substrate, may be formed from the same first filament used to form the substrate and/or may be formed using a different second filament. The second filament may be a monofilament or multifilament. The second filament may be made from any biocompatible, bioabsorbable, or non-bioabsorbable material, including those described herein. In some embodiments, the first and second filaments may be made from the same materials. In other embodiments, the first and second filaments may be made from different materials. For example, in some embodiments, the biocompatible substrate may be formed from at least one first filament made from a non-bioabsorbable material, e.g., polypropylene, polyethylene terephthalate, polytetrafluoroethylene, and the grip-members may be formed from at least one second filament made from a bioabsorbable material, i.e., polylactic acid, polyglycolic acid, and the like.

The grip-members may include any configuration of filaments which extend from the substrate in a manner which aids the substrate to attach to tissue and/or other portions of the implant. Some non-limiting examples of grip-member configurations include loops, hooks, spiked naps, barbed loops, barbed hooks, barbed spiked naps and combinations thereof. The grip-members may be disposed in various arrangements along any portion of the substrate. The grip-members may be formed using any suitable method, including but not limited to, injection molding, stamping, cutting, laser, ultrasonics, melting, and combinations thereof. In embodiments wherein the grip-members include barbs, the barbs may be uni-directional, multi-directional, symmetrical, non-symmetrical, and combinations thereof.

The second filaments used to form the grip-members may be barbed at any time during the manufacturing of the implants described herein. In some embodiments, the second filaments may be barbed prior to being incorporated into the biocompatible substrate. In some embodiments, the second filaments may be barbed after being incorporated into the biocompatible substrate. In still other embodiments the second filaments may be barbed while being incorporated into the biocompatible substrate.

In certain embodiments, the grip-members may be made form second filaments added to the substrate as loops which extend from at least one surface of a biocompatible substrate in a generally perpendicular manner. In other embodiments, the grip-members may be made from a plurality of second filaments which individually extend from the surface of a biocompatible substrate in a generally perpendicular manner. By generally perpendicular, the grip-members may protrude from the surface of the substrate at about 90 degrees. In embodiments, the grip-members may protrude from the surface of the substrate from about 45 to about 135 degrees, and in embodiments from about 60 to about 120 degrees. In still other embodiments, the grip-members may extend from a side-surface of the substrate. In such embodiments, the grip-members may extend along the longitudinal axis of the substrate. In still other embodiments, the substrates may include grip-members which extend from a combination of surfaces and/or directions of the implant.

Figure 1:
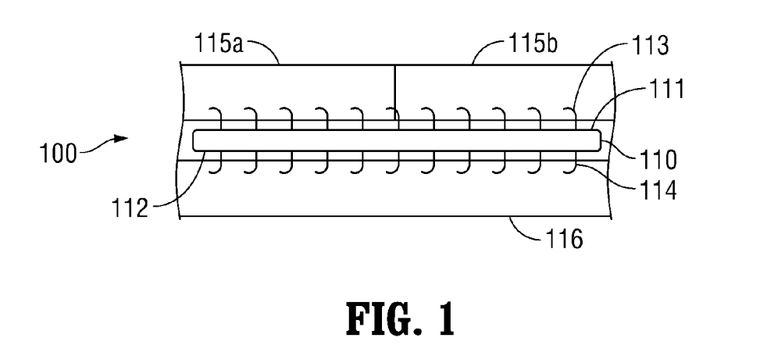
FIG. 1 is a side view of an implantable medical device according to one embodiment described in the present disclosure.

Referring now to FIG. 1, which illustrates implantable medical device 100 which contains biocompatible substrate 110 having first surface 111 and second surface 112. At least one first grip-member 113 extends from first surface 111 of substrate 110 and at least one second grip-member 114 extends from second surface 112 of substrate 110. As shown in FIG. 1, implant 100 may be positioned between approximated tissues 115a and 115b and an underlying layer of tissue 116 to support and/or reinforce the approximated tissue. Since first and second grip-members 113, 114, respectively, have the ability to penetrate some portion of tissues 115a, 115b and 116, there may be no need to further penetrate the tissues with the likes of staples, sutures, clips, adhesives and the like to maintain the approximated tissues 115a, 115b and/or to secure the implant in the tissues. Although grip-members 113 and 114 may appear facing one direction, it is envisioned that grip-members 113 and 114 may be uni-directional, bi-directional and/or multi-directional.

Figure 2:
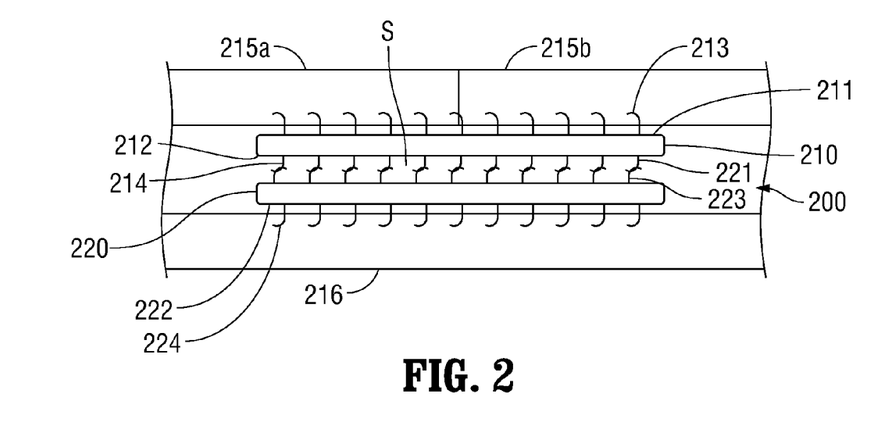
FIG. 2 is a side view of an implantable medical device according to another embodiment described in the present disclosure.

In embodiments, the implantable medical devices described herein may be combined to form multi-planar implants. For example, as depicted in FIG. 2, implantable medical device 200 includes first biocompatible substrate 210 and second biocompatible substrate 220. First biocompatible substrate 210 includes first surface 211 having a plurality of first grip-members 213 and second surface 212 having a plurality of second grip-members 214. Second biocompatible substrate 220 includes third surface 221 having a plurality of third grip-members 223 and fourth surface 222 having a plurality of fourth grip-members 224. As further depicted in FIG. 2, second and third grip-members 214, 223 are interlocked connecting first substrate 210 to second substrate 220. First and second substrates 210, 220 are vertically aligned between tissues 215a, 215b and 216.

In embodiments, the space S between the first and second substrates wherein the grip-members interlock is more susceptible to tissue in-growth than either of the porous substrates and as such may allow the tissue to grow more rapidly in space S. It is further envisioned that the rapid ingrowth of space S will not only assist with interlocking of the grip-members, but also the anchoring of the porous substrates.

In embodiments, the first and second substrates may be removably attached. In embodiments, the first and second substrates may be combined by a surgeon at the site of implantation and/or during the surgical procedure.

In some instances, the thickness of the tissue may be similar to the thickness of an implant as shown in FIG. 1 which includes a single substrate. In some embodiments, as shown in FIG. 2, the implantable medical devices described herein may include more than one substrate to accommodate the varying thickness of certain tissues and or wounds in the tissue.

Figure 3:
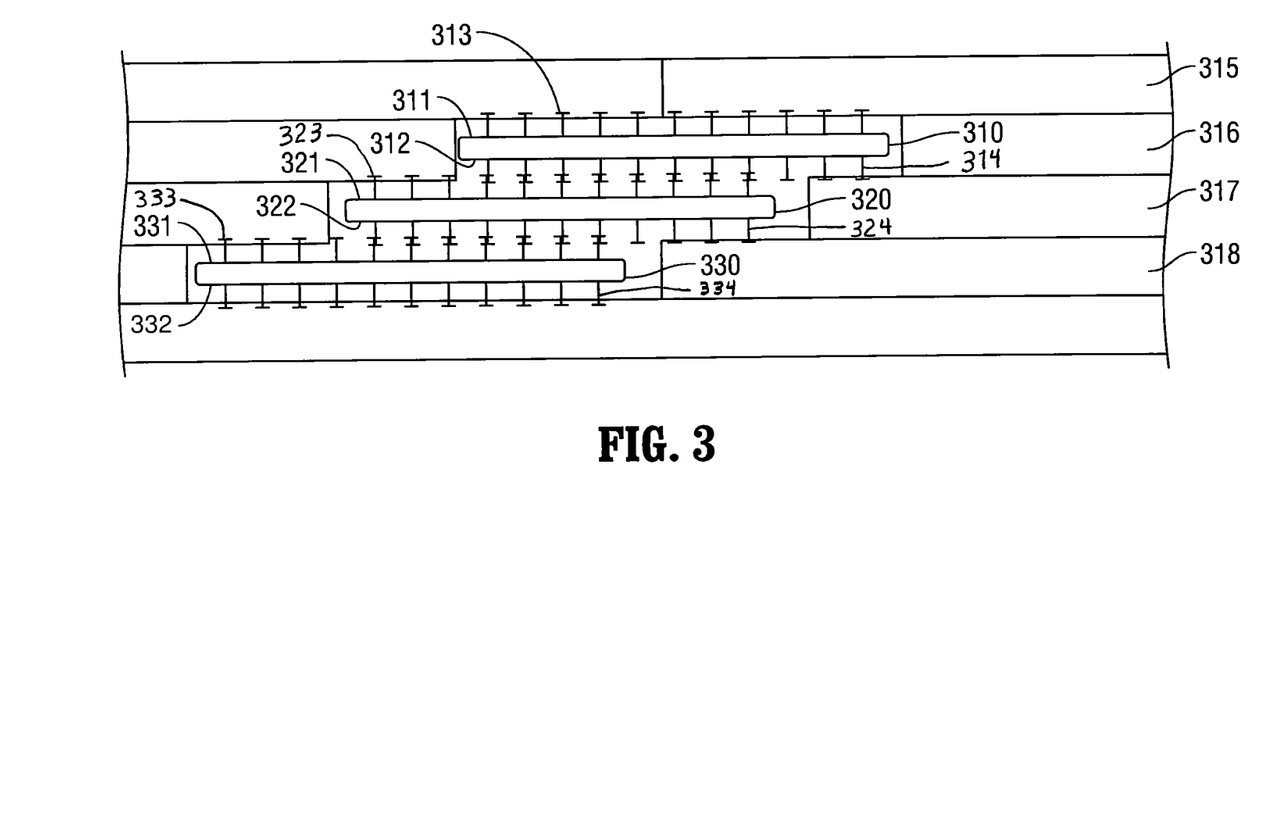
FIG. 3 is a side view of an implantable medical device according to yet another embodiment described in the present disclosure.

In still other embodiments, as shown in FIG. 3 for example, openings and/or wounds tissue may span more than a single layer. In embodiments, openings and/or wounds in tissue may vary in dimensions and may not necessarily be symmetrical. In embodiments, implantable medical device 300 may include a plurality of substrates, 310, 320, and 330, each substrate including at least two surfaces 311, 312, 321, 322, 331, 332 which contain grip-members 313, 314, 323, 324, 333, 334. As illustrated in FIG. 3, the first, second and third substrates 310, 320, and 330, respectively, are not vertically aligned but rather staggered and/or in a step configuration. The wound extends through several layers of tissue 315, 316, 317 and 318 in a diagonal, stepped and/or non-perpendicular manner. In some embodiments, first substrate 310 is smaller in area than second substrate 320 or third substrate 330.

As further illustrated in FIG. 3, some of second and third grip-members 314, 323 are interlocked and connect first and second substrates 310, 320 and some of second and third grip-members 314, 323 are not interlocked and are exposed to attach to tissue layers 316 and 317. Fourth and fifth grip-members 324, 333 are interlocked and connect second and third substrates 320, 330 and some of fourth and fifth grip-members 324, 333 are not interlocked and are exposed to attach to tissue layers 317 and 318.

Figure 4:
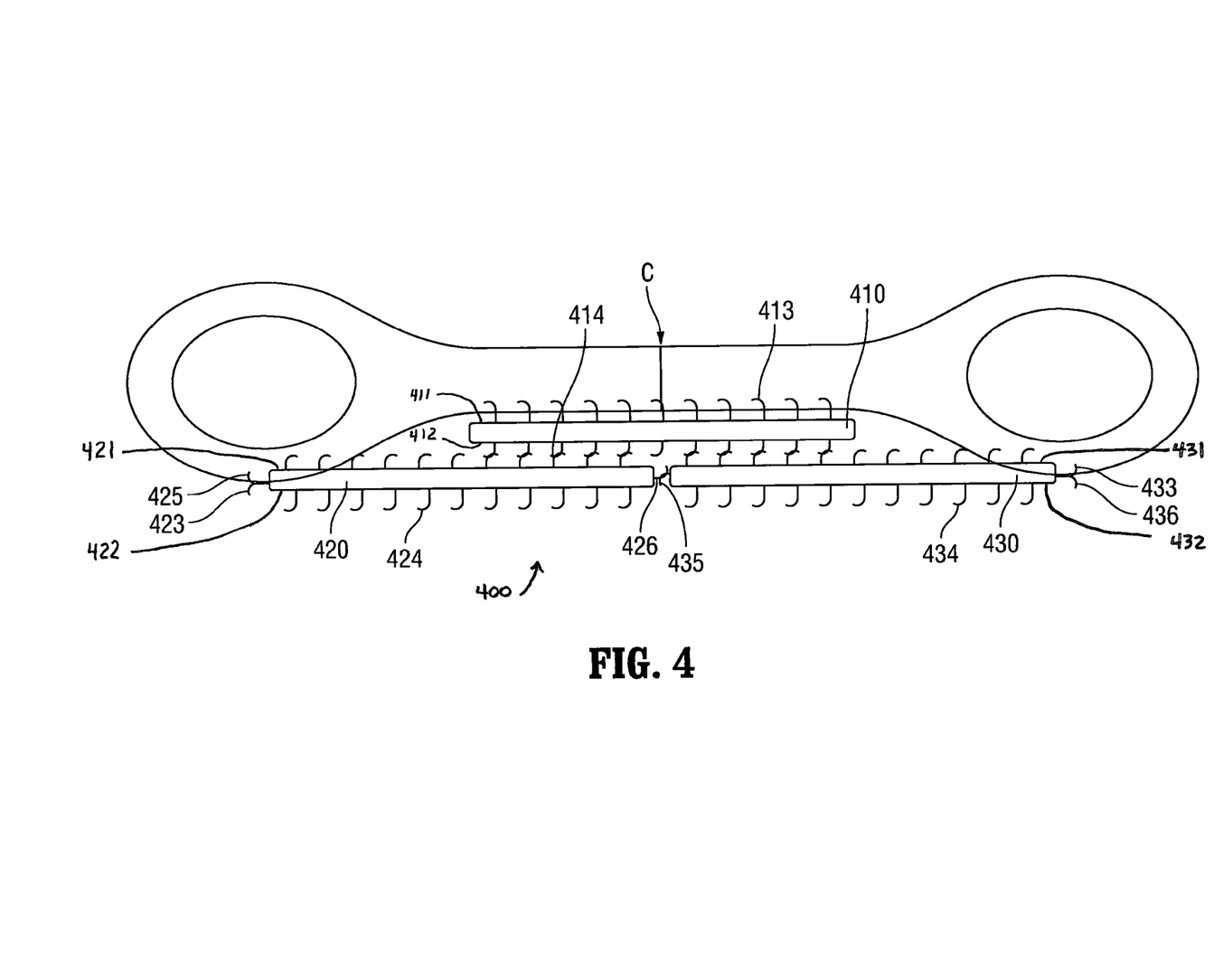
FIG. 4 is a side view of an implantable medical device according to still another embodiment described in the present disclosure.

In still other embodiments, as depicted in FIG. 4, the implants described herein may be used to a midline closure. Implant 400 includes first substrate 410, second substrate, 420, and third substrate 430, wherein second and third substrate 420, 430, respectively, are horizontally aligned and first substrate 410 is positioned across point C wherein second and third substrates 420, 430 are connected. First substrate 410 includes top surface 411 and bottom surface 412 which include first and second grip-members 413, 414, respectively. Second substrate 420 includes second top surface 421 and second bottom surface 422 which include third and fourth grip-members 423, 424, respectively. Third substrate 430 includes third top surface 431 and third bottom surface 432 which includes fifth and sixth grip-members 433, 434, respectively. In addition, second substrate 420 and third substrate 430 further include side grip-members 425, 426, 435, 436 which are positioned along an outer edge of the substrate. As depicted in FIG. 4, the side grip-members may allow multiple substrates to attach and align horizontally and/or further attach the implants described herein to the tissue. In instances where the tissue is not generally planar and/or symmetrical, it is envisioned that the addition of side-grip-members may further stabilize the implants in the tissue.

Figure 5:
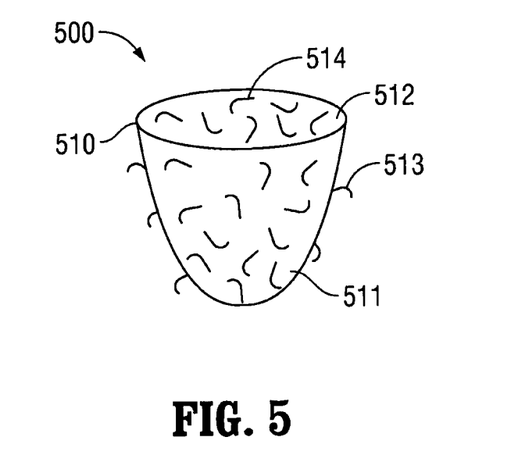
FIG. 5 is a perspective view of an implantable medical device according to still another embodiment described in the present disclosure.

As shown in FIGS. 1-4, the implants described herein may include at least one substrate which is generally planar. In some embodiments, such as those shown in FIGS. 5 and 6, the implants described herein may also include at least one non-planar substrate. In FIG. 5, implant 500 includes first substrate 510 which includes outer surface 511 having a first set of grip-members 513 and inner surface 512 having a second set of grip-members 514. Although shown as a generally conical configuration, it is envisioned that other non-planar configurations may be utilized in forming the implants described herein.

Figure 6:
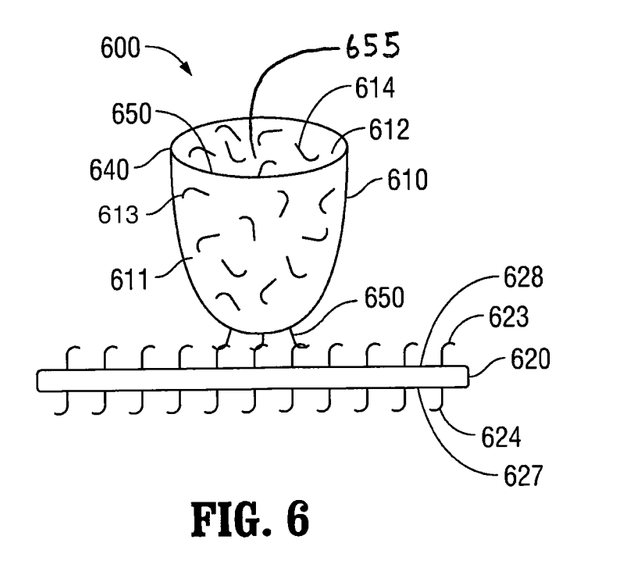
FIG. 6 is a perspective view of an implantable medical device according to still another embodiment described in the present disclosure.

In FIG. 6, first substrate 610 is non-planar and second substrate 620 is generally planar. First substrate 610 includes outer surface 611 containing first grip-members 613 and inner surface 612 including second grip-members 614. First substrate 610 further includes top edge 640, bottom 650 and opening 655 which extends from top edge 640 to bottom 650 and is defined by inner surface 612. Second substrate 620 includes third and fourth grip-members 623, 624. As shown in FIG. 6, first grip-members 613 may be connected to third grip-members 623 to form implant 600.

It is envisioned that in other embodiments the grip-members may comprise the entire surface of the implant. In still other embodiments, the grip-members may be arranged only at the corners of the implant. In yet another embodiment, the concentration of grip-members may vary along different portions of the substrates. Other arrangements of the grip-members are possible and should be apparent to one skilled in the art.

Although the planar substrates are shown to be generally rectangular, the substrates described herein may be of any shape including elliptical, square, triangular, hexagonal, and circular and the like. In addition, the substrate may include apertures to accommodate the passage of bodily tissue when implanted. The implant can be shaped and sized during manufacturing or can be cut to a particular size and shape immediately before use.

Figure 7:
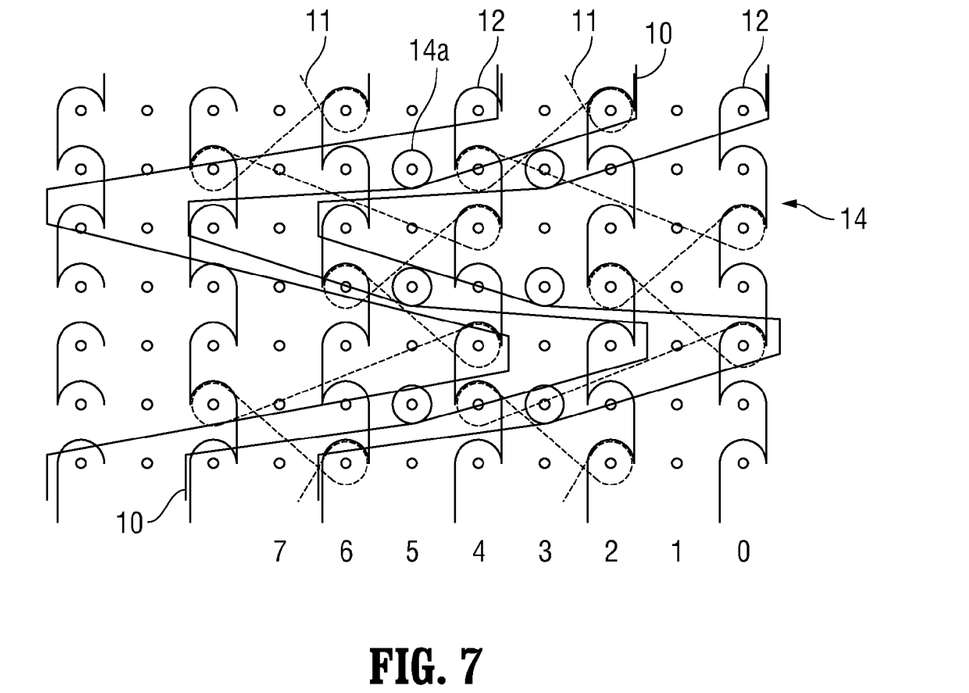
FIG. 7 is a diagram showing a weave pattern for forming an implantable medical device according to an embodiment described in the present disclosure; and, FIGS. 8 and 9 are diagrammatic side views of a device permitting the formation of grip-members on a surface of an implantable medical device described herein.

In certain embodiments, the implantable medical device may be a surgical mesh which made from a plurality of first and second filaments woven in any suitable manner that allows the filaments to form a substrate and form loops or naps which extend from at least one surface of said substrate. FIG. 7 diagrams one representative pattern that will form grip-members in accordance with the present disclosure. The implantable medical device may be made on a warp knitting machine, of the tricot or Raschel type, with at least three sheets or warps of yarn and as many guide bars.

The front and intermediate guide-bars may be threaded with a first set of filaments or yarns. The intermediate bars may be threaded, one guide full, three guides empty, with monofilament or multifilament yarn. This yarn may be made from any suitable biocompatible material; and in some embodiments, may be made from polyethylene terephthalate. This filament or yarn is represented by a broken line and by reference number 11 in FIG. 7. The intermediate bar works in such a way as to obtain a zigzag openwork pattern between the columns of meshes.

The front bar is threaded; one guide full, one guide empty, and works in chain weave with a multifilament or monofilament yarn, represented by number 12 in FIG. 7. The chain stitch imprisons the monofilament 10 and maintains the knit in length while contributing to the formation of the knit with the intermediate sheet formed by yarn 11.

The rear bar may be threaded, one guide full and one guide empty, with a second filament, i.e., monofilament or multifilament. This second filament or yarn may be made from any suitable biocompatible material; and in some embodiments, may be made from polylactic acid.

The diameter of the second filament is over 0.10 millimeter. In practice, this diameter is between 0.14 and 0.18 millimeter and is of the order of 0.15 millimeter. This yarn or filament is represented by reference number 10 and in a solid line in FIG. 7.

The different filaments may be worked according to the following chart:

| Warp | | |
|---|---|---|
| Rear bar I | Intermediate bar II Raschel | Front bar III |
| Front bar II | Intermediate bar II | Rear bar III |
| 7 | 3 | 1 |
| 7 | 2 | 0 |
| — | — | — |
| 3 | 4 | 0 |
| 4 | 5 | 1 |
| — | — | |
| 0 | 1 | |
| 0 | 0 | |
| — | — | |
| 4 | 2 | |
| 3 | 3 | |
| | — | |
| | 1 | |
| | 0 | |
| | — | |
| | 4 | |
| | 5 | |

The rear bar places the yarn in partial weft under the chain stitch and "thrown" onto the needle not forming a chain stitch. For this reason, at the next row, the needle not forming a chain stitch not being supplied permits escape of the monofilament mesh which forms a loop 14a (see also FIGS. 8 and 9) projecting from at least one surface of the medical device.

The medical device thus obtained may be a knit 14 provided with loops 14a which are generally perpendicular to one of the surfaces of the substrate. The loops 14a also display the rigidity to hold at about a right angle, which is obtained by the rigidity or nerve of the second filament employed. This rigidity or nerve may be necessary for the subsequent formation of the spiked naps, barbed spiked naps, hooks, barbed hooks, and/or barbed loops which ensure a tissue-gripping function.

Other patterns by which to obtain a knit with grip-members that protrude from at least one surface should be apparent to one skilled in the art. For example, the knit described herein may be stitched with loops on at least two surfaces of the mesh (FIG. 9) In other embodiments, two knits with grip-members protruding from one surface may be combined to form the implants described herein which include a substrate having grip-members on two or more surfaces. The two or more knits may be combined using any method known to those skilled in the art including, adhesives, stitching, stapling, clips, and the like. In embodiments, a single knit may be knitted which provides loops on both sides of a single knit.

Figure 8:
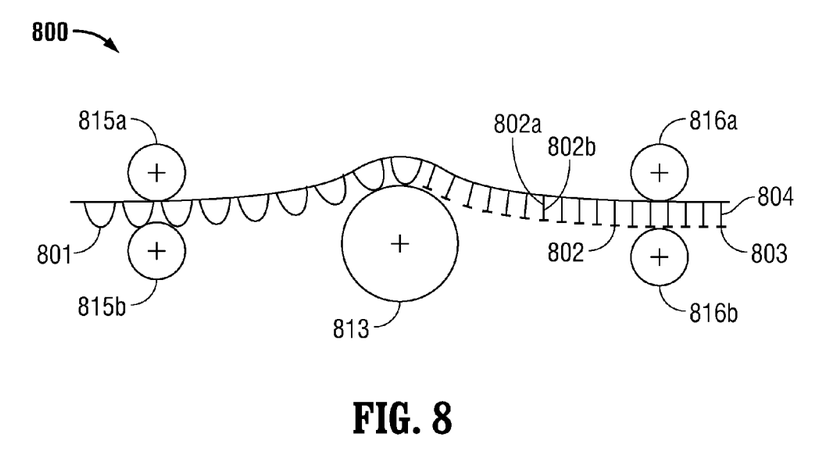

FIG. 8 illustrates one method by which the grip-members can be converted from loops 801 into spiked and naps 802. In one embodiment, the method includes passing substrate 800 with loops 801 over cylinder 813 containing an electrical heating resistor. Substrate 800 may be pressed flat on cylinder 813 by two pairs of rollers, upstream 815a, 815b and downstream 816a, 816b, respectively, which may be vertically displaceable for controlling the pressing force. This control as well as that of the temperature of the resistor placed in cylinder 813 and of the speed of movement of substrate 800 across cylinder 813 make it possible to melt the head of each of the loops 801 so that each loop 801 forms two spiked naps 802.

Each spiked nap 802 thus has a substantially rectilinear body 804 protruding perpendicularly with respect to the substrate 800. Rectilinear body 804 includes attached end 802a and free end 802b, with free end 802b having spike 803 of greater width than that of the body 804. Spike 803 may have the shape of a sphere or mushroom.

Figure 9:
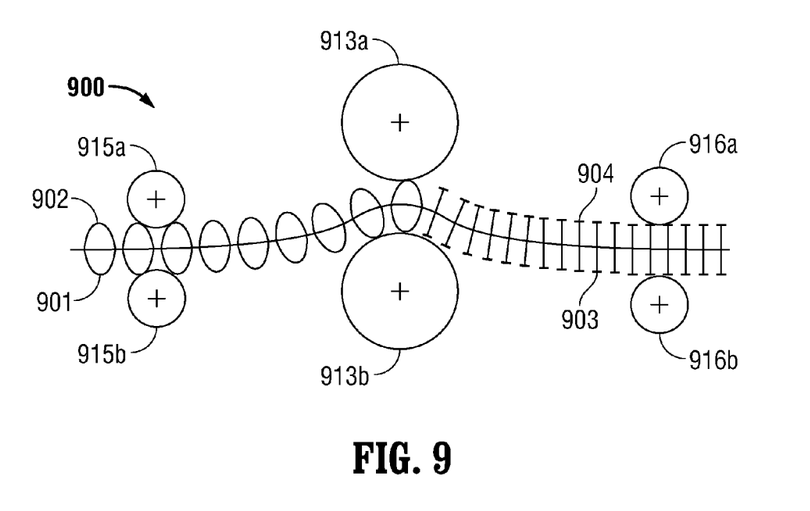

FIG. 9 illustrates one method by which the grip-members can be converted from loops 901, 902 into spiked and naps 903, 904. In one embodiment, the method includes passing substrate 900 with loops 901, 902 over cylinders 913a, 913b containing an electrical heating resistor. Substrate 900 may be pressed flat on cylinders 913a, 913b by two pairs of rollers, upstream 915a, 915b and downstream 916a, 916b, respectively, which may be vertically displaceable for controlling the pressing force. This control as well as that of the temperature of the resistor placed in cylinders 913a, 913b and of the speed of movement of substrate 900 across cylinders 913a, 913b make it possible to melt the head of each of the loops 901, 902 so that each loop 901, 902 forms two spiked naps 903, 904.

In embodiments, the substrate and/or grip-members of the implantable medical device can be combined with and/or coated with a bioactive agent. The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent that provides a therapeutic or prophylactic effect, a compound that effects or participates in tissue growth, cell growth, cell differentiation, and an anti-adhesive compound, a compound that may be able to invoke a biological action such as an immune response, or could play any other role in one or more biological processes. It is envisioned that the bioactive agent may be applied to the substrate and/or loops or naps in any suitable form, e.g., films, powders, liquids, gels, and the like.

Examples of classes of bioactive agents, which may be utilized in accordance with the present disclosure include: anti-adhesives; antimicrobials; analgesics; antipyretics; anesthetics; antiepileptics; antihistamines; anti-inflammatories; cardiovascular drugs; diagnostic agents; sympathomimetics; cholinomimetics; antimuscarinics; antispasmodics; hormones; growth factors; muscle relaxants; adrenergic neuron blockers; antineoplastics; immunogenic agents; immunosuppressants; gastrointestinal drugs; diuretics; steroids; lipids; lipopolysaccharides; polysaccharides; platelet activating drugs; clotting factors; and enzymes. It is also intended that combinations of bioactive agents may be used.

Anti-adhesive agents can be used to prevent adhesions from forming between the implant and the surrounding tissues opposite the target tissue. In addition, anti-adhesive agents may be used to prevent adhesions from forming between the coated implantable medical device and the packaging material. In embodiments, the anti-adhesive agent may be a separate additional layer positioned along some portion of the implant. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent include: triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin, tetracycline; aminoglycosides, such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil, nonoxynol 9, fusidic acid, cephalosporins; and combinations thereof. In addition, antimicrobial proteins and peptides such as bovine lactoferrin and lactoferricin B may be included as a bioactive agent.

Other bioactive agents, which may be included as a bioactive agent include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents, which may be included in the mesh or suture include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

It will be apparent from the foregoing that, while particular forms of the implantable medical devices have been illustrated and described, various modifications can be made without departing from the spirit and scope of the present disclosure. For example, although particular barb configurations may be illustrated and described herein, any suitable configuration and arrangement may be possible.

What is claimed is:

1. An implantable medical device for supporting tissue comprising:
   a first surgical mesh having a planar configuration and including a first top surface including a plurality of first filamentary grip-members and a first bottom surface including a plurality of second filamentary grip-members;
   a second surgical mesh having a planar configuration and including a second top surface including a plurality of third filamentary grip-members and a second bottom surface including a plurality of fourth filamentary grip-members, wherein the first bottom surface of the first surgical mesh is attached to the second top surface of the second surgical mesh via the second and third filamentary grip-members; and
   a third surgical mesh having a planar configuration and including a third top surface including a plurality of fifth filamentary grip-members and a third bottom surface including a plurality of sixth filamentary grip-members, wherein the first and third surgical mesh are vertically staggered and the second and third surgical mesh are horizontally aligned in the same plane.

2. The implantable medical device of claim 1, wherein the first surgical mesh is smaller in area than the second surgical mesh.

3. The implantable medical device of claim 1, wherein the first and second surgical mesh are staggered.

4. The implantable medical device of claim 3, wherein a first portion of the second filamentary grip-members and a first portion of the third filamentary grip-members connect the first bottom surface to the second top surface, and a second portion of the third filamentary grip-members attach a second portion of the second top surface to tissue.

5. The implantable medical device of claim 1, wherein the first filamentary grip-members connect the first top surface to tissue.

6. The implantable medical device of claim 1, wherein a second portion of the second filamentary grip-members and a first portion of the fifth filamentary grip-members interlock to connect a second portion of the first bottom surface to a first portion of the third top surface.

7. The implantable medical device of claim 6, wherein a second portion of the fifth filamentary grip-members connects a second portion of the third top surface to tissue.

8. The implantable medical device of claim 7, wherein the second surgical mesh further includes second side filamentary grip-members positioned along an outer edge of the second surgical mesh, wherein the second side filamentary grip-members connect the second surgical mesh to at least one of the third surgical mesh or tissue.

9. The implantable medical device of claim 8, wherein the third surgical mesh further includes third side filamentary grip-members positioned along an outer edge of the third surgical mesh wherein the third side filamentary grip-members connect the third surgical mesh to at least one of the second surgical mesh or tissue.

10. The implantable medical device of claim 9, wherein the second side filamentary grip-members of the second surgical mesh connect to the third side filamentary grip-members of the third surgical mesh.

11. The implantable medical device of claim 1, wherein the first, second, and third surgical mesh each consist essentially of a plurality of filaments.

12. An implantable medical device for supporting tissue comprising:
   a first substrate having a first top surface including a plurality of first grip-members and a first bottom surface including a plurality of second grip-members; and
   a second substrate having a second top surface including a plurality of third grip-members, a second bottom surface including a plurality of fourth grip-members and a second side surface between the second top surface and the second bottom surface, wherein the first bottom surface of the first substrate is attached to the second top surface of the second substrate via the second and third grip-members a third substrate having a third top surface including a plurality of fifth grip-members and a third bottom surface including a plurality of sixth grip-members, wherein the third top surface of the third substrate is attached to at least one of the first or second substrates, wherein the second substrate further includes second side grip-members positioned along the second side surface of the second substrate, wherein the second side grip-members connect the second side surface of the second substrate to at least one of the third substrate or tissue.

13. The implantable medical device of claim 12, wherein the first substrate is smaller in area than the second substrate.

14. The implantable medical device of claim 12, wherein the first and at least one of the second or third substrates are staggered.

15. The implantable medical device of claim 14, wherein the second and third substrates are horizontally aligned in the same plane.

16. The implantable medical device of claim 15, wherein a first portion of the second grip-members and a first portion of the third grip-members connect the first bottom surface to the second top surface, and a second portion of the third grip-members attach a second portion of the second top surface to tissue.

17. The implantable medical device of claim 12, wherein a second portion of the second grip-members and a first portion of the fifth grip-members interlock to connect a second portion of the first bottom surface to a first portion of the third top surface, and a second portion of the fifth grip-members connects a second portion of the third top surface to tissue.

18. The implantable medical device of claim 12, wherein the third substrate further includes third side grip-members positioned along an outer edge of the third substrate wherein the third side grip-members connect the third substrate to at least one of the second substrate or tissue.

19. The implantable medical device of claim 18, wherein the second side grip-members of the second substrate connect to the third side grip-members of the third substrate.

20. The implantable medical device of claim 12, wherein the first, second, and third substrates each have a planar configuration.

* * * * *